United States Patent [19]

Varadaraj et al.

[11] Patent Number: 5,436,160
[45] Date of Patent: Jul. 25, 1995

[54] BIOREMEDIATION OF HYDROCARBON CONTAMINATED SOIL

[75] Inventors: Ramesh Varadaraj, Flemington; Jan Bock, Warren; Max L. Robbins, South Orange, all of N.J.

[73] Assignee: Exxon Research & Engineering Co., Florham Park, N.J.

[21] Appl. No.: 190,391

[22] Filed: Feb. 2, 1994

[51] Int. Cl.$^6$ .................... C10G 32/00; C02F 3/00; C02F 3/34
[52] U.S. Cl. .................... 435/264; 435/262; 435/281; 435/262.5
[58] Field of Search ............. 435/264, 281, 262, 262.5

[56] References Cited

U.S. PATENT DOCUMENTS

| | | | |
|---|---|---|---|
| 3,616,204 | 10/1971 | Linn | 435/281 |
| 4,146,470 | 3/1979 | Mohfin et al. | 435/281 |
| 5,128,262 | 7/1992 | Lindoerfer et al. | 435/264 |

*Primary Examiner*—Herbert J. Lilling
*Attorney, Agent, or Firm*—Joseph J. Dvorak

[57] ABSTRACT

The bioremediation of hydrocarbon contaminated soil is enhanced by applying to the soil a hydrocarbon solution of a surfactant selected from the group consisting of: (a) mixture of a sorbitan ester of a $C_7$ to $C_{22}$ monocarboxylic acid and a polyoxyalkylene adduct of a sorbitan monoester of a $C_7$ to $C_{22}$ monocarboxylic acid, the adduct having from 6 to 50 polyoxyalkylene units, (b) an alkyl glycoside wherein the alkyl group has from about 8 to about 18 carbon atoms and the glycoside is a mono or diglycoside and (c) a mixture of (a) and (b) and (c) and thereafter applying microbial nutrients to the soil in amounts sufficient to promote the growth of indigenous microorganisms.

12 Claims, No Drawings

BIOREMEDIATION OF HYDROCARBON CONTAMINATED SOIL

FIELD OF THE INVENTION

The present invention relates to microbial remediation of hydrocarbon contaminated soil and especially oil contaminated soil.

BACKGROUND OF THE INVENTION

Microorganisms present in soil are known to assimilate hydrocarbons but, unfortunately, at such a slow rate that natural biodegradation of hydrocarbon contaminated soil is not a practical soil remediation method. Attempts to accelerate microbial growth to enhance soil remediation typically involve providing microbial nutrient material, especially nitrogen and phosphorous containing nutrient materials to the contaminated soil. While the addition of microbial nutrients to contaminated soil is somewhat beneficial, the rate of hydrocarbon biodegradation still remains inadequate to be a totally practical soil bioremediation technique. Therefore, there remains a need for improvements in techniques for enhancing the microbial bioremediation of hydrocarbon contaminated soil.

Apparently, petroleum contaminants, and especially weathered petroleum soil contaminants, are not readily accessible to the microorganisms capable of assimilating the contaminant. Additionally, it would appear that the extent of microbial utilization of petroleum hydrocarbons is further limited by the number and activity of hydrocarbon assimilating microflora.

Accordingly, the present invention provides an improved method for enhancing the bioremediation of hydrocarbon contaminated soil by stimulating the growth and activity of naturally occurring, hydrocarbon assimilating, microflora and by rendering the hydrocarbon contaminant more accessible to the microflora.

SUMMARY OF THE INVENTION

In one embodiment of the present invention, the bioremediation of hydrocarbon contaminated soil is enhanced by applying to the soil a hydrocarbon solution of a surfactant selected from the group consisting of: (a) mixture of a sorbitan ester of a $C_7$ to $C_{22}$ monocarboxylic acid and a polyoxyalkylene adduct of a sorbitan ester of a $C_7$ to $C_{22}$ monocarboxylic acid, the adduct having from 4 to 50 polyoxyalkylene units, (b) an alkyl glycoside wherein the alkyl group has from about 8 to about 18 carbon atoms and the glycoside is a mono or diglycoside, or mixtures thereof, and (c) a mixture of (a) and (b) and thereafter applying microbial nutrients to the soil in amounts sufficient to promote the growth of indigenous microorganisms.

In another embodiment at least the top of the soil is mixed after the solution is applied, for example, by tilling, plowing, disking and the like.

In a preferred embodiment of the present invention, the above solution is applied to the soil at a rate from about 1 to 30 weight percent of solution based on the weight of hydrocarbon contaminant in the soil.

These and other embodiments of the present invention will be described in greater detailed description which follows.

DETAILED DESCRIPTION OF THE INVENTION

For convenience, in the description which follows specific mention will be made to enhancing the bioremediation of an oil contaminated soil. It should be readily appreciated, however, that the invention is not limited to enhancing the bioremediation solely of oil contaminated soil, but any hydrocarbon contaminated soil that is capable of being biodegraded can also be treated in accordance with the methods detailed herein.

In the practice of the present invention, bioremediation of oil contaminated soil is enhanced by first applying to the soil a hydrocarbon solution of a surfactant selected from the group consisting of: (a) a mixture of surfactants selected from monocarboxylic acid esters of sorbitan and polyoxyalkylene adducts of monocarboxylic acid esters of sorbitan, (b) alkyl glycosides and (c) mixtures of (a) and (b). In general the sorbitan carboxylic acids forming the esters will have from 7 to 22 carbon atoms. The polyoxyalkylene groups will range from 4 to 50 units per adduct and preferably will be selected from polyoxyethylene and polyoxypropylene groups. In the case of alkyl glycosides, the alkyl groups will have from about 8 to about 18 carbon atoms and the glycoside is a mono or diglucoside or a mixture thereof.

In general, the surfactant is dissolved in a normal or branched aliphatic hydrocarbon having from about 6 to about 16 carbon atoms, although hydrocarbons such as tetralin, cycloalkanes, alkyl substituted aromatics and terpenes may also be employed as a solvent.

Generally, when the surfactant is a mixture of the above described sorbitan, they are combined to provide a HLB (Hydrophilic-Lipophilic Balance) in the range of from 4.5 to about 12.5.

Typically, the surfactant used will constitute from about 15 to about 75 weight percent of the total weight of solution.

In the practice of the invention, the solution of the surfactant in the hydrocarbon solvent is applied to the soil typically by pouring, spraying, broadcasting and the like. Typically, the amount of solution applied to the soil will depend upon the amount of hydrocarbon contaminant in the soil. In general however, the amount of solution to be applied, may range for example from about 1 percent by weight to about 30 percent by weight and preferably about 10 percent by weight based on the amount of contamination oil in the soil.

After application of the surfactant solution to the soil, it is preferred to mix, at least the top surface of the soil, for example the top 6 to 24 inches, by any convenient means such as plowing, tilling, disking, roto-tilling and the like. In appropriate cases, however, the soil can be charged into a mechanical mixer and mixed with the solution therein. Thereafter, microbial nutrients may be applied to the soil by any convenient means such as broadcasting pellets, powders, and the like in and by spraying solutions of the nutrients; however, in the practice of the present invention it is preferred that microbial nutrients are applied by spraying an aqueous solution of the nutrients on the soil to be treated.

Typical microbial nutrients include urea, potassium nitrate, ammonium nitrate, and ammonium phosphate, sodium phosphate, and the like. In general, these nutrients are applied at a rate to provide a carbon to nitrogen to phosphorous ratio in the soil in the range of about 100:1:0.1 to about 100:10:5 and preferably 100:2:0.2.

After application of the microbial nutrients preferably they are then mixed with the soil, again by any convenient means such as plowing, tilling, disking, rototilling and the like.

In an alternate embodiment of the invention, the surfactants solution and nutrients can be applied to the soil concurrently or sequentially, followed by mixing. In a preferred embodiment of the invention the treated soil is periodically mixed and watered to maintain its water content, at least in the top 6 inches, in the range of from about 10 wt % to about 25 wt %.

To further illustrate the present invention, reference is made to the following examples:

EXAMPLES 1–3

In the following examples, three separate pans of hydrocarbon contaminated soil, 12 inches long by 8 inches wide and 3 inches deep were treated with a solution of a mixture sorbitans described in greater detail below. In each case the mixture of surfactants constituted 50 wt % percent of the solution with the solvent being Norpar-13, which is the trademark for a relatively narrow boiling range solvent sold by Exxon Company USA, Houston, Tex. Norpar-13 contains greater than 98% by weight of normal paraffins. In these examples, the sorbitan carboxylic acid ester applied in the surfactant solution was a sorbitan mono-oleate sold under the trade name Span-80 by ICI Americas, Wilmington, Del. The polyoxylene sorbitan mono-ester employed was a polyoxyethylene (20) sorbitan mono-oleate sold under the trade name Tween-80, also by ICI Americas. In examples 1 and 2, the ratio of Span 80 to Tween-80 provided an HLB of 6.9, in example 3, the HLB was 9.5.

In example 1, the solution was applied to the soil at the rate of 10% weight percent based on the weight of hydrocarbon contaminant in the soil. In example 2, the treat rate was 3 times that of example 1. The surfactant solution was then mixed with the soil by hand-tilling. Next an aqueous solution of urea and ammonium dihydrogen phosphate having a C:N:P ratio of 100:2:0.2 was applied to the soil followed by hand-tilling. The pans were watered and hand-tilled weekly. The amount of water applied was sufficient to provide a moisture content of about 17 wt. %

After two, four, and six week periods, the percent petroleum hydrocarbons biodegraded was determined for each of the examples using EPA method 418.1 with the following modifications.

1. The soil sample size was increased to 30 grams.
2. The acidification step specified in the test was eliminated.
3. The amount of drying agent required by the test was increased to assure effective drying.
4. The drying agent used was magnesium sulfate.
5. A four hour time period for soxhlet extraction was employed.
6. The amount of silica gel used was increased.

Also the microbial population was determined on the soil samples two weeks after treatment. The standard most probable number (MPN) microbiology method was employed and a two week incubation period was allowed. Results of these tests are shown in the following Table, which for comparative purposes also includes the results obtained in two comparative examples.

COMPARATIVE EXAMPLES 1 AND 2

In comparative example 1, the soil was not treated. The amount of petroleum hydrocarbon biodegraded over time as well as the amount of heterotrophs was determined as outlined above. In comparative example 2, the soil was treated solely with an aqueous solution of urea and ammonium dihydrogen phosphate followed by mixing. Thereafter, the percent of petroleum hydrocarbon biodegraded was determined in two, four, and six week intervals as described above. Also, the microbial population numbers were determined as in example 1 to 3.

Table

| Example | Treatment Type | % Hydrocarbon Biodegraded | | | Microbial Population (MPN) Heterotrophs |
|---|---|---|---|---|---|
| | | 2 wk | 4 wk | 6 wk | |
| Comparative 1 | None | 0.0 | 2.0 | 1.0 | $1.68 \times 10^2$ |
| Comparative 2 | Nutrient Only | 9.5 | 9.5 | 12.18 | $1.38 \times 10^4$ |
| Example 1 | Span-80/ Tween-80 Norpar-13 (HLB 6.9) and nutrient | 19.9 | 31.0 | 37.4 | $1.95 \times 10^9$ |
| Example 2 | Span-80/ Tween-80 Norpar-13 (HLB 6.9) and nutrient | 21.0 | 29.3 | 36.1 | N.D. |
| Example 3 | Span-80/ Tween-80 Norpar-13 (HLB 9.5) and nutrient | 19.2 | 30.4 | 38.5 | $5.54 \times 10^9$ |

ND = Not determined

What is claimed is:

1. A method for improving bioremediation of hydrocarbon contaminated soil with indigenous micro organisms by applying to hydrocarbon contaminated soil a hydrocarbon solution of a surfactant selected from the group consisting of (a) a mixture of a sorbitan ester of a $C_7$ to $C_{22}$ monocarboxylic acid and a polyoxyalkylene adduct of a sorbitan monoester of a $C_7$ to $C_{22}$ monocarboxylic acid, the adduct having from 6 to 50 polyoxyalkylene units, (b) alkyl glycoside wherein the alkyl group has from about 8 to about 18 carbon atoms and the glycoside is a mono or diglycoside, and (c) a mixture of (a) and (b), the solution being applied in amounts sufficient to promote the growth of indigenous micro organisms.

2. The method of claim 1 including applying microbial nutrients to the soil.

3. The method of claim 2 wherein the solution and nutrients are applied sequentially.

4. The method of claim 3 wherein the soil is mixed after applying the solution.

5. The method of claim 4 wherein the soil is mixed after applying the nutrients.

6. The method of claim 1 wherein the hydrocarbon solvent is selected from the group consisting of linear and branched aliphatic hydrocarbons, cycloalkanes, aromatics, and alkyl aromatics having 6 to 16 carbon atoms and terpenes.

7. The method of claim 6 wherein the solution contains from about 15 to about 75 wt. % of surfactant.

8. The method of claim 1 wherein the solution is applied at a rate to provide 1 wt. % to 30 wt. % of surfactant based on the weight of hydrocarbon contaminant in the soil.

9. The method of claim 2 wherein the microbial nutrients are applied in aqueous solution.

10. The method of claim 9 including maintaining the moisture content of the soil that is mixed, in the range of from about 10 wt. % to about 25 wt. %.

11. A method for increasing the rate of biodegradation of hydrocarbon contaminants in soil by indigenous micro organisms comprising: applying to the soil a hydrocarbon solution of a surfactant selected from (a) a mixture of a sorbitan ester of a $C_7$ to $C_{22}$ monocarboxylic acid and a polyoxyalkylene adduct of a sorbitan ester of a $C_7$ to $C_{22}$ monocarboxylic acid, the adduct having from 6 to 50 polyoxyalkylene units, (b) a alkyl mono or diglycoside or mixtures thereof having about 8 to about 18 carbon atoms in the alkyl group, and (c) mixtures of (a) and (b), the solution containing about 15 wt. % to about 75 wt. % of surfactant, the surfactant applied at a rate of about 1 to about 30 wt. % based on the weight of hydrocarbon contaminant in the soil;

mixing at least the top surface of the soil;

applying an aqueous solution of microbial nutrients to the mixed soil at a rate to provide a C:N:P ratio in the soil in the range of from about 100:1:0:1 to about 100:10:5; and thereafter mixing the top surface of the soil, whereby the rate of biodegradation of hydrocarbon contaminants is increased.

12. The method of claim 11 including periodically adding water to the soil in an amount sufficient to provide a soil moisture content of from about 10 wt. % to about 25 wt. %.

* * * * *